United States Patent
Baxter et al.

(10) Patent No.: US 9,442,058 B2
(45) Date of Patent: Sep. 13, 2016

(54) METHODS, SYSTEMS, AND APPARATUS FOR GENERATING A GAS STREAM HAVING A DESIRED PARTICULATE MATERIAL CONCENTRATION

(75) Inventors: Robert Wyatt Baxter, Raleigh, NC (US); Derrick James Hinkle, Louisburg, NC (US); Edward Lee Salter, Youngsviille, NC (US); Ralph Edward Bard, Raleigh, NC (US)

(73) Assignee: B3 Systems, Inc., Raleigh, NC (US)

( * ) Notice: Subject to any disclaimer, the term of this patent is extended or adjusted under 35 U.S.C. 154(b) by 654 days.

(21) Appl. No.: 13/153,072

(22) Filed: Jun. 3, 2011

(65) Prior Publication Data
US 2012/0304730 A1 Dec. 6, 2012

(51) Int. Cl.
*G01N 15/00* (2006.01)
*G01N 15/06* (2006.01)
*G01N 15/10* (2006.01)
*G01N 1/28* (2006.01)

(52) U.S. Cl.
CPC .............. *G01N 15/06* (2013.01); *G01N 15/00* (2013.01); *G01N 15/1012* (2013.01); *G01N 2001/2893* (2013.01); *G01N 2015/0046* (2013.01)

(58) Field of Classification Search
CPC ..................... G01N 15/06; G01N 2015/0046
USPC ......................................................... 73/1.03
See application file for complete search history.

(56) References Cited

U.S. PATENT DOCUMENTS

| | | | | |
|---|---|---|---|---|
| 2,985,120 A | * | 5/1961 | Brandt | B65F 3/18 110/222 |
| 2002/0144535 A1 | * | 10/2002 | Sakata et al. | 73/1.03 |
| 2003/0029221 A1 | * | 2/2003 | Juneau et al. | 73/1.02 |
| 2003/0101916 A1 | * | 6/2003 | Brown | F23G 1/00 110/194 |
| 2010/0255437 A1 | * | 10/2010 | Gibson | F27B 19/00 432/11 |

OTHER PUBLICATIONS

U.S. Environmental Protection Agency, Technology Transfer Network Emission Measurement Center, "Performance Specification 11—Specifications and Test Procedures for Particulate Matter Continuous Emission Monitoring Systems at Stationary Sources", Aug. 10, 2011, 28 Pages, Retrieved from URL at http://www.epa.gov/ttnemc01/perfspec.html on Nov. 20, 2013.

* cited by examiner

*Primary Examiner* — Paul West
(74) *Attorney, Agent, or Firm* — Myers Bigel & Sibley, P.A.

(57) ABSTRACT

A method validating a particulate monitoring device includes generating a final gas stream having a particulate material concentration that corresponds to a target particulate material concentration, using the particulate monitoring device to measure the particulate material concentration in the final gas stream, and evaluating an accuracy of the particulate monitoring device based on a comparison of the particulate concentration in the final gas stream that was measured by the particulate monitoring device with the target particulate material concentration.

21 Claims, 4 Drawing Sheets

```
                          Begin
                            │
                            ▼
        ┌─────────────────────────────────────┐  ╱ 400
        │   Provide feed of particulate material │╱
        └─────────────────────────────────────┘
                            │
                            ▼
        ┌─────────────────────────────────────┐  ╱ 410
        │  Mix feed of particulate material with │╱
        │  first gas flow in first mixing chamber│
        └─────────────────────────────────────┘
                            │
                            ▼
        ┌─────────────────────────────────────┐  ╱ 420
        │    Discharge at least a portion of the │╱
        │      first gas stream into a second    │
        │    mixing chamber based on a target    │
        │     particulate material concentration │
        └─────────────────────────────────────┘
                            │
                            ▼
        ┌─────────────────────────────────────┐  ╱ 430
        │  Mix second gas stream with second     │╱
        │  gas flow in second mixing chamber     │
        │  to generate final gas stream having   │
        │  a particulate material concentration  │
        │    that corresponds to the target      │
        │     particulate material concentration │
        └─────────────────────────────────────┘
                            │
                            ▼
                           End
```

*FIG. 4*

METHODS, SYSTEMS, AND APPARATUS FOR GENERATING A GAS STREAM HAVING A DESIRED PARTICULATE MATERIAL CONCENTRATION

BACKGROUND

The present disclosure relates generally to monitoring of particulate discharge and, more particularly, to methods, systems, and apparatus that can be used to audit and/or calibrate particulate monitoring devices.

A variety of suspended particles may be found in a typical atmosphere whether indoor or outdoor. Size, chemical composition, concentration, and temporal variability all have the potential to affect public health and perception of pollution. As a result, particulate monitoring devices or instruments are becoming more prevalent in both process and environmental applications. The increased use of particulate monitoring devices/instruments may require that the devices/instruments undergo more stringent auditing for particular monitoring applications and/or to develop application specific calibration curves to improve the accuracy of the devices/instruments. In this regard, initiatives may be taken to improve the accuracy of a particulate monitoring device that include, but are not limited to, development of calibration curves based on a range of particulate concentrations, verification of existing calibration curves, and verifying/documenting an instrument's response. Conventional techniques for auditing and/or calibrating a particulate material monitoring device/instrument typically involve installing the particular monitoring device/instrument at a source site where the particulate material is generated. The installed particulate monitoring instrument's output is compared with the results of an existing reference method that provide the particulate material concentration in a plant's stack or duct. Unfortunately, these conventional techniques generally require the particulate monitoring instrument to be first installed at the source site and, therefore, cannot be used to audit and/or calibrate the particulate monitoring instrument offsite at a potentially more convenient location.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the disclosure.

Some embodiments provide a method validating a particulate monitoring device comprising generating a final gas stream having a particulate material concentration that corresponds to a target particulate material concentration, using the particulate monitoring device to measure the particulate material concentration in the final gas stream, and evaluating an accuracy of the particulate monitoring device based on a comparison of the particulate concentration in the final gas stream that was measured by the particulate monitoring device with the target particulate material concentration.

In other embodiments, generating the final gas stream comprises providing a feed of particulate material and mixing the feed of particulate material with a gas flow in a mixing chamber to generate the final gas stream.

In still other embodiments, the gas flow is a first gas flow, the mixing chamber is a first mixing chamber, and mixing the feed of particulate material with the first gas flow in the first mixing chamber generates a first gas stream, and wherein generating the final gas stream further comprises discharging at least a portion of the first gas stream into a second mixing chamber based on a target particulate material concentration to generate a second gas stream, and mixing the second gas stream with a second gas flow in the second mixing chamber to generate the final gas stream.

In still other embodiments, providing the feed of particulate material comprises providing source particulate material and dividing the source particulate material into the feed of particulate material and a diverted portion of source particulate material.

In still other embodiments, dividing the source particulate material comprises dividing the source particulate material based on the target particulate material concentration.

In still other embodiments, the method further comprises weighing the source particulate material and weighing the diverted portion of the source particulate material. Dividing the source particulate material comprises dividing the source particulate material until a difference in weight between the source particulate material and the diverted portion of the source particulate material is about equal to a target weight difference.

In still other embodiments, discharging the at least the portion of the first gas stream into the second mixing chamber comprises discharging the first gas stream in its entirety into the second mixing chamber.

In still other embodiments, discharging the at least the portion of the first gas stream into the second mixing chamber comprises dividing the first gas stream into the second gas stream and a diverted portion of the first gas stream.

In still other embodiments, the method further comprises determining a flow rate of the second gas stream and determining a particulate material concentration in the second gas stream. Dividing the first gas stream comprises dividing the first gas stream into the second gas stream and the diverted portion of the first gas stream based on the flow rate of the second gas stream and the particulate material concentration in the second gas stream.

In still other embodiments, generating the final gas stream comprises using a mobile system to generate the final gas stream.

In still other embodiments, the particulate monitoring device is associated with a site that generates native particulate material and the particulate material comprises the native particulate material generated at the site.

In still other embodiments, the particulate monitoring device is associated with a site that generates native particulate material and the particulate material comprises reference particulate material, separate from the native particulate material, having a composition based on requirements associated with the site.

In still other embodiments, the method further comprises determining the particulate material concentration in the final gas stream corresponds to the target particulate material concentration using a trusted methodology.

In still other embodiments, determining the particulate material concentration in the final gas stream using a trusted methodology comprises using a calibrated particulate monitoring device to measure the particulate material concentration in the final gas stream.

In still other embodiments, the target particulate material concentration is a first target particulate material concentration, the method further comprising generating the final gas stream having the particulate material concentration that corresponds to a second target particulate material concentration and performing the using of the particulate monitoring device to measure the particulate material concentration in the final gas stream and the evaluating of the accuracy of the particulate monitoring device responsive to generating the final gas stream having the particulate material concentration that corresponds to the second target particulate material concentration.

Further embodiments provide a system comprising apparatus configured to generate a final gas stream having a particulate material concentration that corresponds to a target particulate material concentration and a particulate monitoring device configured to measure the particulate material concentration in the final gas stream.

In still further embodiments, the system further comprises a validator configured to evaluate an accuracy of the particulate monitoring device based on a comparison of the particulate concentration in the final gas stream that was measured by the particulate monitoring device with the target particulate material concentration.

In still further embodiments, the apparatus comprises a feeder that is configured to provide a feed of particulate material and a mixing chamber that is configured to mix mixing the feed of particulate material with a gas flow in a mixing chamber to generate the final gas stream.

In still further embodiments, the gas flow is a first gas flow, the mixing chamber is a first mixing chamber, mixing the feed of particulate material with the first gas flow in the first mixing chamber generates a first gas stream, the first mixing chamber is further configured to discharge at least a portion of the first gas stream based on a target particulate material concentration to generate a second gas stream, and the apparatus further comprises a second mixing chamber that is configured to receive the second gas stream and to mix the second gas stream with a second gas flow in the second mixing chamber to generate a final gas stream having a particulate material concentration that corresponds to the target particulate material concentration.

In still further embodiments, the feeder comprises a splitting unit that is configured to divide source particulate material into the feed of particulate material and a diverted portion of source particulate material.

In still further embodiments, the splitting unit is configured to divide the source particulate material based on the target particulate material concentration.

In still further embodiments, the system further comprises a first scale that is configured to weigh the source particulate material and a second scale that is configured to weigh the diverted portion of the source particulate material. The splitting unit is configured to divide the source particulate material until a difference in weight between the source particulate material and the diverted portion of the source particulate material is about equal to a target weight difference.

In still further embodiments, the first mixing chamber is further configured to discharge the first gas stream in its entirety into the second mixing chamber.

In still further embodiments, the first mixing chamber is further configured to discharge the at least the portion of the first gas stream into the second mixing chamber by dividing the first gas stream into the second gas stream and a diverted portion of the first gas stream.

In still further embodiments, the first mixing chamber is further configured to determine a flow rate of the second gas stream, determine a particulate material concentration in the second gas stream, and divide the first gas stream into the second gas stream and the diverted portion of the first gas stream based on the flow rate of the second gas stream and the particulate material concentration in the second gas stream.

In still further embodiments, the apparatus is a mobile apparatus.

In still further embodiments, the system further comprises apparatus configured to determine that the particulate material concentration in the final gas stream corresponds to the target particulate material concentration using a trusted methodology.

In still further embodiments, the apparatus configured to determine that the particulate material concentration in the final gas stream comprises a calibrated particulate monitoring device configured to measure the particulate material concentration in the final gas stream.

In still further embodiments, the particulate monitoring device is associated with a site that generates native particulate material and wherein the particulate material comprises native particulate material generated at the site.

In still further embodiments, the particulate monitoring device is associated with a site that generates native particulate material and wherein the particulate material comprises reference particulate material, separate from the native particulate material, having a composition based on requirements associated with the site.

Other methods, systems, and/or apparatus according to embodiments of the invention will be or become apparent to one with skill in the art upon review of the following drawings and detailed description. It is intended that all such additional methods, systems, and/or apparatus be included within this description, be within the scope of the present invention, and be protected by the accompanying claims.

BRIEF DESCRIPTION OF THE DRAWINGS

Other features of exemplary embodiments will be more readily understood from the following detailed description of specific embodiments thereof when read in conjunction with the accompanying drawings, in which:

FIG. 1 is a block diagram that illustrates a system for generating a gas stream having a particulate material concentration that corresponds to a target particulate material concentration according to some embodiments of the present invention;

FIG. 2 is a flowchart that illustrates a method of generating a gas stream containing a target particulate material concentration according to some embodiments of the present invention;

FIG. 3 is a block diagram that illustrates a system for generating a gas stream having a particulate material concentration that corresponds to a target particulate material concentration according to further embodiments of the present invention; and FIG. 4 is a flowchart that illustrates a method of generating a gas stream containing a target particulate material concentration according to further embodiments of the present invention.

DETAILED DESCRIPTION

While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention as defined by the claims. Like reference numbers signify like elements throughout the description of the figures.

As used herein, the singular forms "a," "an," and "the" are intended to include the plural forms as well, unless expressly stated otherwise. It should be further understood that the terms "comprises" and/or "comprising" when used in this specification is taken to specify the presence of stated features, integers, steps, operations, elements, and/or components, but does not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Embodiments are described herein with respect to generating a gas stream that contains a particulate material. It will be understood that the particulate material is not limited to any type of material and may include, but is not limited to, solid materials, particles, dust, and the like.

Some embodiments described herein are based on the concept of providing a gas stream with a known particulate material concentration that can then be used to audit and/or calibrate a particulate material monitoring device. In contrast to conventional systems, however, a system for generating a gas stream containing a particulate material according to embodiments of the present invention may be mobile and, thus, can be used to calibrate a particulate material monitoring device off site or the system can be transported to a site to calibrate one or more particulate material monitoring devices. The particulate material monitoring device's response to various concentrations of particulate material generated by the system according to embodiments of the present invention can be used to develop initial calibration curves, verify existing calibration curves, or document the device's response. Various materials can be used as the particulate material in the generated gas stream including native materials, such as ash, fly ash, product, etc. from a site to develop a site specific response for a particulate material monitoring device or a non-native material that may be devised based on site requirements, for example, to test a standard response for a particulate monitoring device to reduce the effect of native materials.

Figure 1:
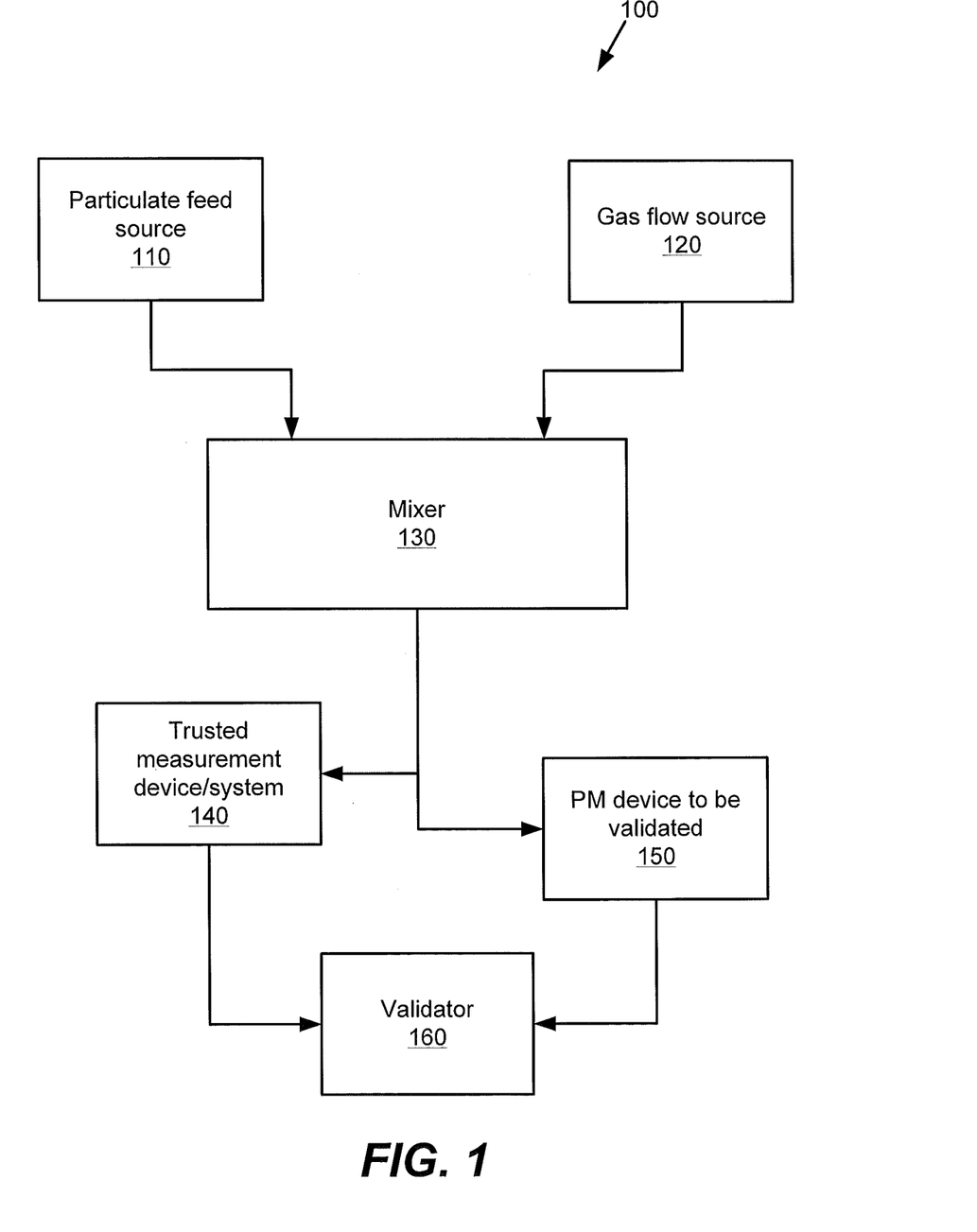

FIG. 1 illustrates a system 100 for generating a gas stream having a target particulate material concentration according to some embodiments of the present invention. As shown in FIG. 1, the system 100 comprises a particulate source feed 110 along with a gas flow source 120 whose outputs are fed into a mixer 130. The flow of particulate from the particulate feed source 110 along with the flow of gas from the gas flow source 120 may be precisely controlled to ensure that the concentration of the particulate matter in the mixer is at a target concentration. For example, techniques, such as using a loss-in-weight feeder, diverting portions of the particulate feed, and the like can be used to control the amount of particulate matter to be mixed with the gas stream in the mixer 130 based on the flow fate of the gas output from the gas flow source 120.

The mixer 130 may be embodied as a chamber that is configured to mix the particulate material feed provided from the particulate source feed 110 with the gas stream output from the gas flow source 120. The purpose of the mixer 130 is to fluidize the particulate material in the gas stream and to accelerate the particulate material to a desired velocity for entrainment. After the particulate material is fluidized, entrained, and mixed in the gas stream, the entire stream is output so as to have a target particulate matter concentration of sufficient accuracy that it can be used to validate the accuracy of a particulate monitoring device.

As shown in FIG. 1, the final gas stream output from the mixer 130, which has a particulate material concentration corresponding to a target particulate material concentration, is provided to a particulate monitoring device 150 to be validated. The particulate monitoring device 150 measures the concentration of the particulate matter in the gas stream and a validator 160 can be used to compare the particulate material concentration measured by the particulate monitoring device 150 with the target particulate material concentration to determine the accuracy of the particulate monitoring device 150. If the particulate monitoring device 150 obtains a measurement different than the target particulate material concentration, then the particulate monitoring device 150 may be re-calibrated to improve the accuracy of its measurement. This process can be repeated for multiple target particulate material concentration to ensure that the particulate monitoring device is producing accurate results over a range of particulate material concentration levels.

In some embodiments, the system 100 may include a trusted measurement device or system 140 that is used to ensure that the system 100 is generating a final gas stream that has a particulate material concentration sufficiently close to the target particulate material concentration. In some embodiments, the trusted measurement device 140 may be a calibrated particulate monitoring device that is trusted to provide accurate measurements of the particulate material concentration in the final gas stream output from the mixer 130. In such embodiments, the validator 160 may compare the measurement taken by the trusted calibrated particulate monitoring device with the measurement taken by the particulate monitoring device 150 to evaluate the accuracy of the particulate monitoring device 150.

FIG. 2 is a flowchart that illustrates a method of generating a gas stream containing a target particulate material concentration based on the system of Claim 1 according to some embodiments of the present invention. Referring to FIG. 2, operations begin at block 200 where the particulate feed source 110, gas flow source 120, and mixer 130 generates a final gas stream that has a particulate material concentration that corresponds to a target particulate material concentration. In some embodiments, a trusted measurement device and/or methodology is used at block 210 to determine ensure that the final gas stream has a particulate material concentration that is sufficiently close to the target particulate material concentration. A particulate monitoring device that is to be validated, e.g., particulate monitoring device 150, is used to measure the particulate material concentration in the final gas stream at block 220. The accuracy of the particulate monitoring device 150 is evaluated at block 230 by comparing the measurement of the particulate material concentration obtained from the particulate monitoring device 150 with the target particulate material concentration generated in the final gas stream output from the mixer 130. In some embodiments, the measurement obtained from the particulate monitoring device 150 may also be compared with a measurement taken by a trusted calibrated particulate monitoring device 140.

Figure 3:
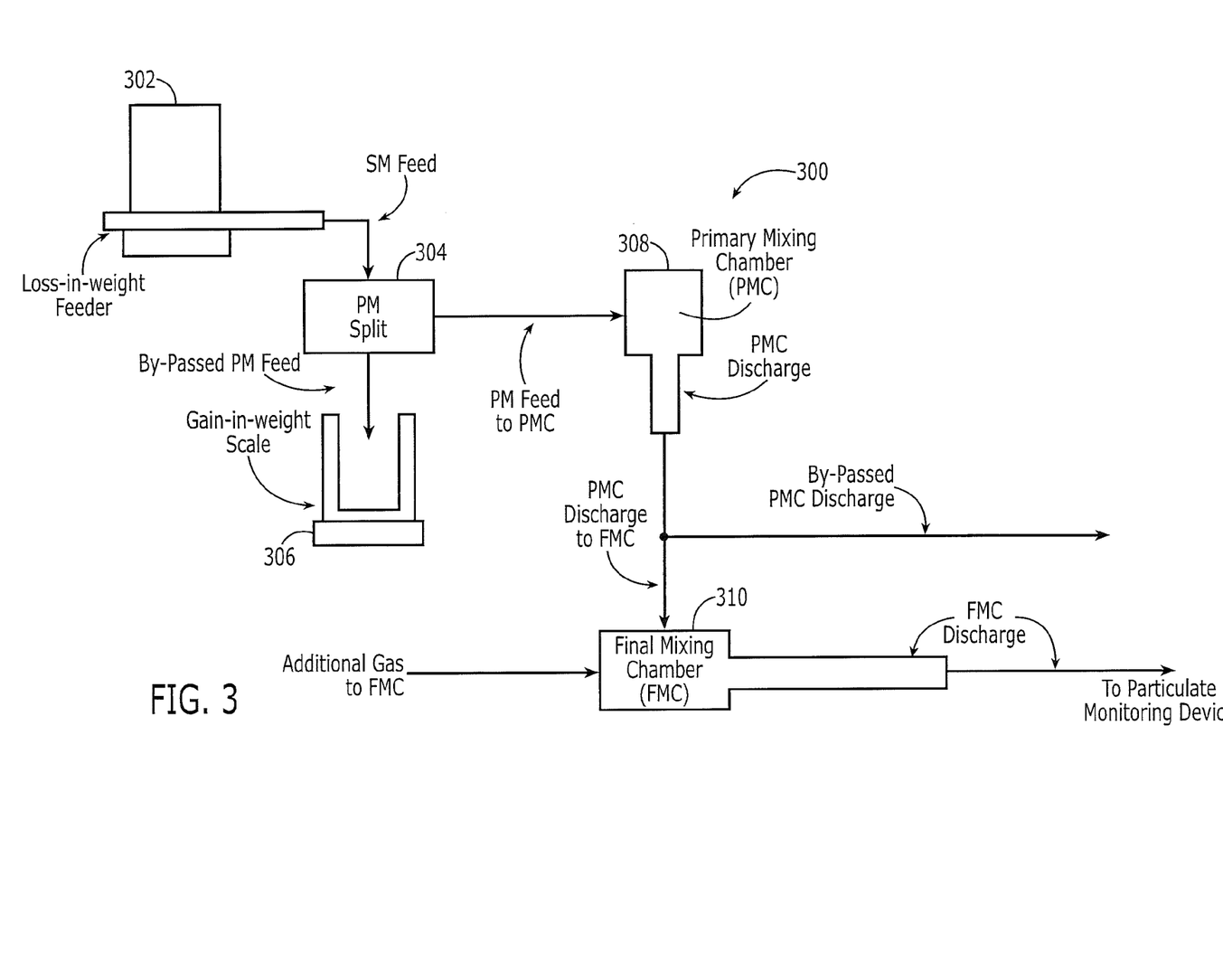

FIG. 3 illustrates a system 300 for generating a gas stream having a target particulate material concentration according to further embodiments of the present invention. As shown in FIG. 3, the system 300 comprises a loss-in-weight feeder 302, a splitting unit 304, a gain-in-weight scale 306, a primary mixing chamber 308, and a final mixing chamber 310, which are connected as shown. The loss-in-weight feeder 302 is used to monitor and control the feed rate of the particulate material into the system 300. The particulate material from the loss-in-weight feeder 302 is discharged into the splitting device 304. The loss-in-weight feeder 302 is used to monitor and adjust the feed rate to maintain a desired final feed rate. For lower desired particulate material concentrations, the splitting device 304 is configured to divert a portion of the source particulate material from the loss-in-weight feeder 302 to the gain-in-weight scale 306.

The gain-in-weight scale 306 may be used to monitor the diverted source particulate material, which can then be compared to the total feed rate of source particulate material from the loss-in-weight feeder 302 to arrive at a desired flow of particulate material into the primary mixing chamber 308. In some embodiments, the gain-in-weight scale 306 collects the diverted particulate material on a scale where it can be weighed. The weight of the diverted source material can be subtracted from the total weight of the source material provided by the loss-in-weight feeder 302 to determine the amount of particulate material being provided to the primary mixing chamber 308.

The primary mixing chamber 308 is configured to mix the particulate material feed provided from the loss-in-weight feeder 302 less any particulate material diverted by the splitting unit 304 with a gas stream. The purpose of the primary mixing chamber 308 is to fluidize the particulate material in a gas stream and to accelerate the particulate material to a desired velocity for entrainment. After the particulate material is fluidized, entrained, and mixed in the gas stream, the entire stream is transported through the primary mixing chamber 308 discharge line.

Based on a desired final particulate material concentration, all or a portion of the gas stream discharged from the primary mixing chamber 308 is provided to the final mixing chamber 310. When a lower particulate material concentration is desired, a portion of the gas stream discharged from the primary mixing chamber 308 may be diverted or bypassed. When a portion of the gas stream discharged from the primary mixing chamber 308 is diverted or bypassed, the primary mixing chamber 308 may include a flow meter after the diversion point to directly monitor the gas stream's flow rate if the particulate matter does not interfere with the flow monitoring. Alternatively, in other embodiments, an indirect method, such as dynamic spiking and analysis of the downstream gases may be used to determine the flow rate of the gas stream provided to the final mixing chamber 310. The primary mixing chamber 308 may further include, in some embodiments, additional instrumentation to monitor the concentration of particulate material in the gas stream to be directed to the final mixing chamber 310 and the diverted gas stream to ensure that they are approximately the same. Such instrumentation may provide a qualitative analysis that provides an indication of the particulate material in the gas stream if no non-destructive (i.e., having no effect on the particulate material concentration) quantitative measuring devices are available. The above-described flow rate monitoring and particulate matter concentration analysis at the output of the primary mixing chamber 308 may be unnecessary if none of the gas flow at the output of the primary mixing chamber 308 is diverted or bypassed.

The gas stream output from the primary mixing chamber 308 less any portion that is diverted or bypassed is provided to the final mixing chamber 310 where it is mixed with an additional gas stream in a way to ensure proper mixing of the particulate material in the stream. The amount of additional gas provided in the final mixing chamber 310 is monitored, metered, and adjusted so as to generate a final gas stream having a particulate material concentration that corresponds to a target particulate material concentration. The final particulate material concentration can be determined by knowing the total flow of the additional gas provided in the final mixing chamber 310 along with the flow rate of the gas stream that is output from the primary mixing chamber 308 less any portion that is diverted or bypassed prior to the final mixing chamber 310.

In accordance with some embodiments of the present invention, both the primary mixing chamber 308 and the final mixing chamber 310 are high velocity, high energy regions that are configured to ensure gas and particulate matter are well mixed. The total gas flow exiting a mixing chamber may be at a rate that will result in a gas velocity high enough to maintain the particulate material in suspension. The minimum acceptable velocity may vary based on the type of particulate material used and, therefore, the gas flow velocities may be monitored throughout the system 300 to ensure that the gas velocity exceeds the minimum acceptable velocity for the type of particulate material being used. One qualitative sign that the gas flow velocity is too low is a settling of particulate material in locations of the system 100 where settling would be unexpected.

For purposes of illustration, a system for generating a gas stream containing a desired particulate material concentration, according to some embodiments of the present invention, has been described above in which two mixing chambers 308 and 310 are used. It will be understood that additional mixing chambers can be used to achieve a desired particulate material concentration in a gas stream. For example, any desired number of mixing chambers may be connected in series in which the particulate material is mixed with a stream and then a portion of the stream output from the mixer is diverted before additional mixing is performed in a subsequent mixer to dilute the concentration of the particulate material in the gas stream down to a desired level.

As described above, various mechanisms may be used in the system 300 to generate a gas stream having a particulate material concentration that is sufficiently close to a target particulate material concentration that it can be used as a reference for auditing and/or calibrating a particulate material monitoring device. Specifically, the system provides for precisely adjusting the amount of particulate material used through use of the loss-in-weight feeder 302, splitting unit 304, and gain-in-weight scale 306. When a portion of the gas stream discharged from the primary mixing chamber 308 is diverted or bypassed, various flow rate monitors and techniques can be used to determine the flow rate of gas to be provided to the final mixing chamber 310 and the concentration of particulate matter in the gas stream to be provided to the final mixing chamber can also be monitored. Finally, additional gas added during in the final mixing chamber 310 can be precisely controlled to ensure that the final gas stream to be used in testing a particulate monitoring device has a particulate material concentration that is sufficiently close to a target concentration that it can be used as a testing standard.

Once the particulate material concentration in the final mixing chamber 310 has reached steady state, testing of a particulate material monitoring device can begin. The connection of the particulate material monitoring device to the output of the final mixing chamber 310 may vary depending on the type of particulate material monitoring device. Some devices may be extractive and may be capable of pulling a sample out of the final gas stream generated by the final mixing chamber 310. Other devices may require special adapters to interface to the final mixing chamber 310. During each test run the device's response may be monitored and logged for the duration of the run. The final particulate matter concentration may be monitored and logged for the duration of the run. The device's average response during the test and the average particulate matter concentration in the final gas stream during the test may be used for evaluating the device's accuracy. As described above, the system 300 may be a mobile system that can be transported from site to site to evaluate particulate material monitoring devices using native particulate material associated with the site or non-native particulate material. Alternatively, device's can be brought to the system 300 for evaluation.

Exemplary embodiments are described herein with reference to flowchart and/or block diagram illustrations of methods, systems, and apparatus in accordance with exemplary embodiments. These flowchart and/or block diagrams further illustrate exemplary operations for generating a gas stream having a particulate material concentration that can be used to audit and/or calibrate particulate monitoring devices in accordance with some embodiments.

Figure 4:
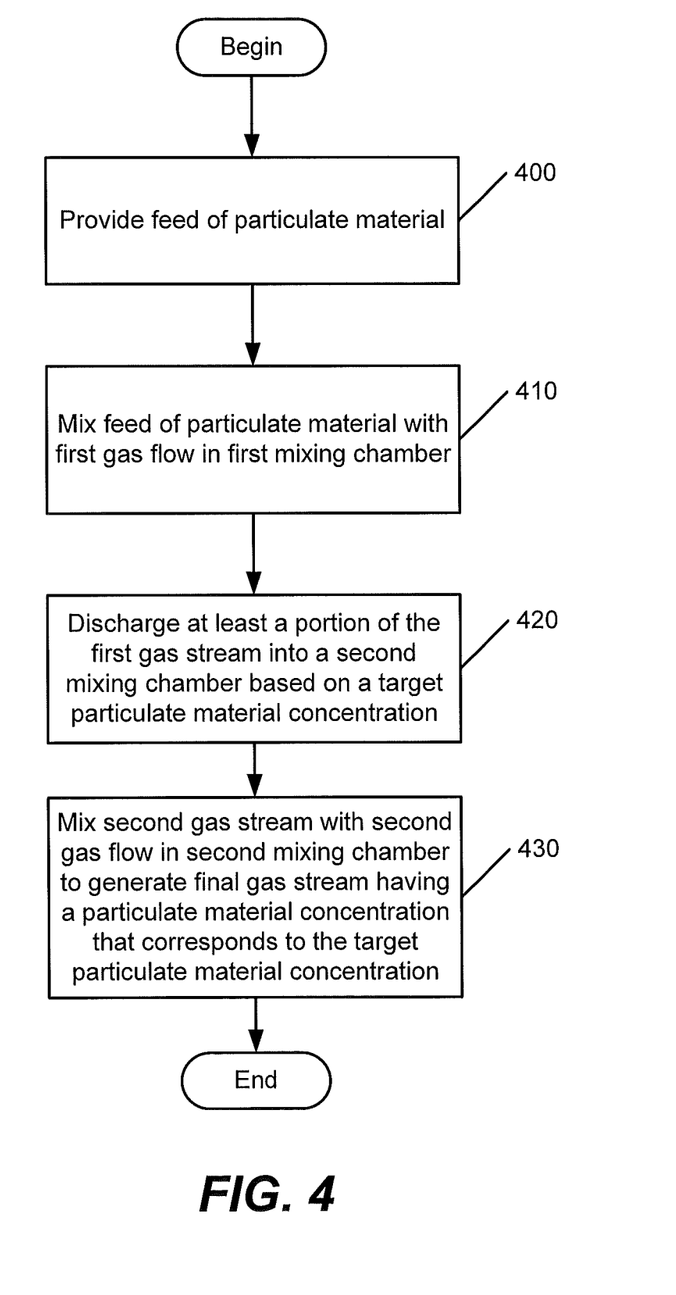

FIG. 4 is a flowchart that illustrates a method of generating a gas stream containing particulate material based on the system of FIG. 3 according to some embodiments of the present invention. Operations begin at block 400 where a feed of particulate material is provided. At block 410, the feed of particulate material is mixed with a first gas flow in a first mixing chamber to generate a first gas stream. At least a portion of the first gas stream is charged into a second mixing chamber at block 420 based on a target particulate material concentration to generate a second gas stream. The second gas stream is mixed with a second gas flow at block 430 to generate a final gas stream having a particulate material concentration that corresponds to the target particulate material concentration.

Figure 2:
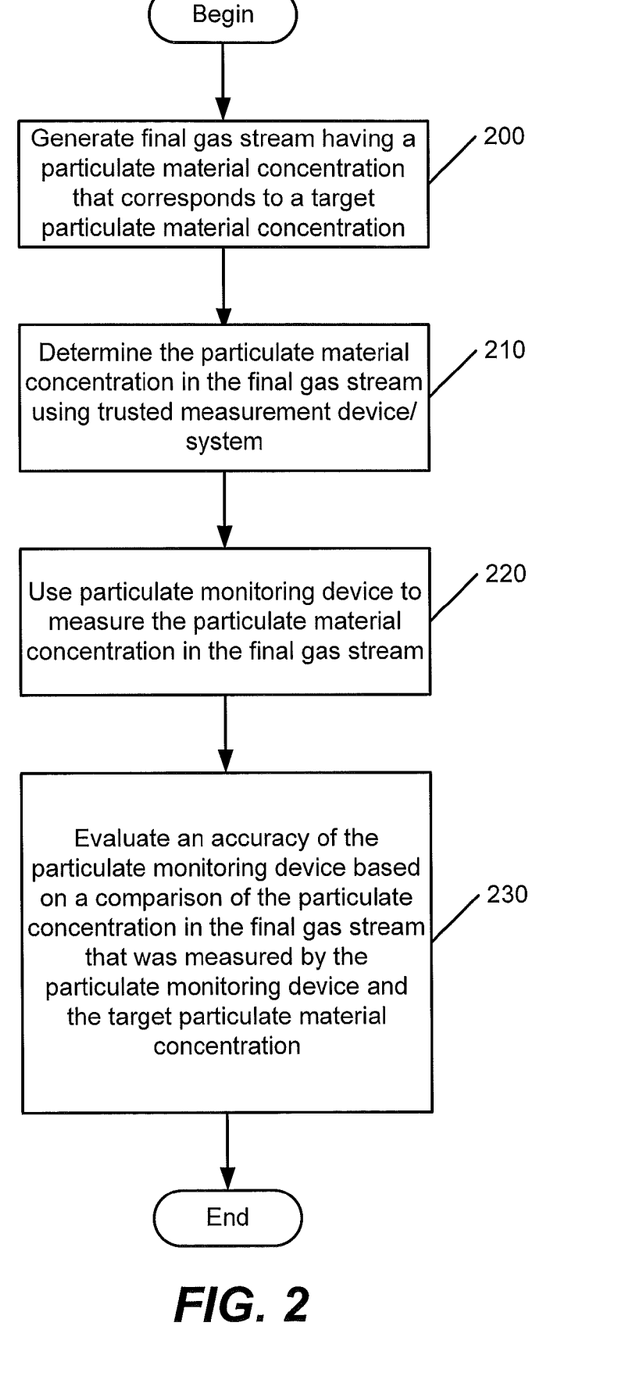

The flowcharts of FIGS. 2 and 4 illustrate the architecture, functionality, and operations of some embodiments of methods, systems, and apparatus for generating a gas stream having a particulate material concentration that can be used to audit and/or calibrate particulate monitoring devices. It should also be noted that in other implementations, the function(s) noted in the blocks may occur out of the order noted in FIGS. 4 and 5. For example, two blocks shown in succession may, in fact, be executed substantially concurrently or the blocks may sometimes be executed in the reverse order, depending on the functionality involved.

Many variations and modifications can be made to the preferred embodiments without substantially departing from the principles of the present invention. All such variations and modifications are intended to be included herein within the scope of the present invention, as set forth in the following claims.

That which is claimed:

1. A method of validating a particulate monitoring device, comprising:
   generating a final gas stream having a target particulate material concentration, the target particulate material concentration being a calculated target particulate material concentration value based on characteristics of the particulate material and the gas without measuring a particulate material concentration in the final gas stream;
   using the particulate monitoring device to measure the particulate material concentration in the final gas stream to generate a measured particulate material concentration value; and
   evaluating an accuracy of the particulate monitoring device based on a direct comparison of the calculated target particulate material concentration value with the measured particulate material concentration value;
   wherein generating the final gas stream comprises:
   providing a feed of particulate material;
   mixing the feed of particulate material with a first gas flow in a first mixing chamber to generate a first gas stream;
   dividing the first gas stream into a diverted portion of the first gas stream and a second, gas stream based on the target particulate material concentration, the second gas stream being discharged into a second mixing chamber; and
   mixing the second gas stream with a second gas flow in the second mixing chamber to generate the final gas stream.

2. The method of claim 1, wherein providing the feed of particulate material comprises:
   providing source particulate material; and
   dividing the source particulate material into the feed of particulate material and a diverted, portion of source particulate material.

3. The method of claim 2, wherein dividing the source particulate material comprises dividing the source particulate material based on the target particulate material concentration.

4. The method of claim 3, further comprising:
   weighing the source particulate material;
   weighing the diverted portion of the source particulate material;
   wherein dividing the source particulate material comprises dividing the source particulate material until a difference in weight between the source particulate material and the diverted portion of the source particulate material is about equal to a target weight difference.

5. The method of claim 1, further comprising:
   determining a flow rate of the second gas stream; and
   determining a particulate material concentration in the second gas stream;
   wherein dividing the first gas stream comprises dividing the first gas stream into the second gas stream and the diverted portion of the first gas stream based on the flow rate of the second gas stream and the particulate material concentration in the second gas stream.

6. The method of claim 1, wherein generating the final gas stream comprises using a mobile system to generate the final gas stream.

7. The method of claim 1, wherein the particulate monitoring device is associated with a site that generates native particulate material and wherein the particulate material comprises the native particulate material generated at the site.

8. The method of claim 1, wherein the particulate monitoring device is associated with a site that generates native particulate material and wherein the particulate material comprises reference particulate material, separate from the native particulate material, having a composition based on requirements associated with the site.

9. A system, comprising:
apparatus configured to generate a final gas stream having a target particulate material concentration, the target particulate material concentration being a calculated target particulate material concentration value based on characteristics of the particulate material and the gas without measuring a particulate material concentration in the final gas stream;
a particulate monitoring device configured to measure the particulate material concentration in the final gas stream to generate a measured particulate material concentration value; and
a validator configured to evaluate an accuracy of the particulate monitoring device based on a direct comparison of the calculated target particulate material concentration value with the measured particulate material concentration value
a feeder that is configured to provide a feed of particulate material;
a first mixing chamber that is configured to mix the feed of particulate material with a first gas flow to generate a first gas stream, the first mixing chamber being further configured to divide the first gas stream into a diverted portion of the first gas stream and a second gas stream based on the target particulate material concentration;
a second mixing chamber, the second gas stream being discharged into the second mixing chamber, which is configured to mix the second gas stream with a second gas flow to generate the final gas stream.

10. The system of claim 9, wherein the feeder comprises a splitting unit that is configured to divide source particulate material into the feed of particulate material and a diverted portion of source particulate material.

11. The system of claim 10, wherein the splitting unit is configured to divide the source particulate material based on the target particulate material concentration.

12. The system of claim 11, further comprising:
a first scale that is configured to weigh the source particulate material; and
a second scale that is configured to weigh the diverted portion of the source particulate material;
wherein the splitting unit is configured to divide the source particulate material until a difference in weight between the source particulate material and the diverted portion of the source particulate material is about equal to a target weight difference.

13. The system of claim 9, wherein the first mixing chamber is further configured to determine a flow rate of the second gas stream, determine a particulate material concentration in the second gas stream, and divide the first gas stream into the second gas stream and the diverted portion of the first gas stream based on the flow rate of the second gas stream and the particulate material concentration in the second gas stream.

14. The system of claim 9, wherein the apparatus is a mobile apparatus.

15. The system of claim 9, wherein the particulate monitoring device is associated with a site that generates native particulate material and wherein the particulate material comprises native particulate material generated at the site.

16. The method of claim 9, wherein the particulate monitoring device is associated with a site that generates native particulate material and wherein the particulate material comprises reference particulate material, separate from the native particulate material, having a composition based on requirements associated with the site.

17. A method of validating a particulate monitoring device, comprising:
generating a final gas stream in a mobile system having a target particulate material concentration, the target particulate material concentration being a calculated target particulate material concentration value based on characteristics of the particulate material and the gas without measuring a particulate material concentration in the final gas stream;
using the particulate monitoring device to measure the particulate material concentration in the final gas stream in the mobile system to generate a measured particulate material concentration value; and
evaluating an accuracy of the particulate monitoring device based on a direct comparison of the calculated target particulate material concentration value with the measured particulate material concentration value;
wherein generating the final gas stream comprises:
providing a feed of particulate material; and
mixing the feed of particulate material with a gas flow in a mixing chamber to generate the final gas stream;
wherein the gas flow is a first gas flow, wherein the mixing chamber is a first mixing chamber, wherein mixing the feed of particulate material with the first gas flow in the first mixing chamber generates a first gas stream, and wherein generating the final gas stream further comprises:
discharging at least a portion of the first gas stream into a second mixing chamber based on a target particulate material concentration to generate a second gas stream; and
mixing the second gas stream with a second gas flow in the second mixing chamber to generate the final gas stream; and
wherein discharging the at least the portion of the first gas stream into the second mixing chamber comprises:
dividing the first gas stream into the second gas stream and a diverted portion of the first gas stream.

18. The method of claim 17, wherein providing the feed of particulate material comprises:
providing source particulate material; and
dividing the source particulate material into the feed of particulate material and a diverted portion of source particulate material.

19. The method of claim 18, wherein dividing the source particulate material comprises dividing the source particulate material based on the target particulate material concentration.

20. The method of claim 19, further comprising:
weighing the source particulate material;
weighing the diverted portion of the source particulate material;
wherein dividing the source particulate material comprises dividing the source particulate material until a difference in weight between the source particulate material and the diverted portion of the source particulate material is about equal to a target weight difference.

21. The method of claim 17, further comprising:
determining a flow rate of the second gas stream; and determining a particulate material concentration in the second gas stream;
wherein dividing the first gas stream comprises dividing the first gas stream into the second gas stream and the diverted portion of the first gas stream based on the flow rate of the second gas stream and the particulate material concentration in the second gas stream.

\* \* \* \* \*

UNITED STATES PATENT AND TRADEMARK OFFICE
CERTIFICATE OF CORRECTION

PATENT NO. : 9,442,058 B2  
APPLICATION NO. : 13/153072  
DATED : September 13, 2016  
INVENTOR(S) : Baxter et al.

Page 1 of 1

It is certified that error appears in the above-identified patent and that said Letters Patent is hereby corrected as shown below:

In the Claims

Column 10, Claim 1, Line 24: Please correct "second, gas" to read -- second gas --

Column 10, Claim 2, Line 35: Please correct "diverted, portion" to read -- diverted portion --

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*